United States Patent
Chen et al.

(10) Patent No.: US 7,780,343 B2
(45) Date of Patent: Aug. 24, 2010

(54) MICROMACHINED GAS AND LIQUID CONCENTRATION SENSOR AND METHOD OF MAKING THE SAME

(75) Inventors: Chih-Chang Chen, Cupertino, CA (US); Yahong Yao, Milpitas, CA (US); Gaofeng Wang, San Jose, CA (US); Liji Huang, San Jose, CA (US)

(73) Assignee: Siargo Ltd., Santa Clara, CA (US)

( * ) Notice: Subject to any disclaimer, the term of this patent is extended or adjusted under 35 U.S.C. 154(b) by 0 days.

(21) Appl. No.: 11/774,771

(22) Filed: Jul. 9, 2007

(65) Prior Publication Data
US 2009/0016403 A1    Jan. 15, 2009

(51) Int. Cl.
*G01N 25/00* (2006.01)
*G01K 3/00* (2006.01)
*G01K 7/00* (2006.01)

(52) U.S. Cl. .................. 374/45; 374/110; 374/183; 374/166; 73/61.46; 73/25.01

(58) Field of Classification Search .......... 374/45, 374/110, 166, 183; 73/25.01, 61.46
See application file for complete search history.

(56) References Cited

U.S. PATENT DOCUMENTS

| 4,902,138 | A  * | 2/1990 | Goeldner et al. ............. 374/44 |
| 4,909,078 | A  * | 3/1990 | Sittler et al. ............. 73/204.26 |
| 6,838,287 | B2 * | 1/2005 | Bonne et al. ................ 436/149 |
| 2008/0092628 | A1* | 4/2008 | Oishi et al. ................ 73/25.01 |
| 2009/0100911 | A1* | 4/2009 | Kawanishi et al. ......... 73/61.43 |

* cited by examiner

*Primary Examiner*—Lisa M Caputo
*Assistant Examiner*—Mirellys Jagan

(57) ABSTRACT

A device with micromachined (a.k.a. MEMS, Micro Electro Mechanical Systems) silicon sensor to measure gas or liquid concentration in a binary mixture formality is disclosed in the present invention. A process for fabricating the said MEMS silicon concentration sensor, which thereby can greatly reduce the sensor fabrication cost by a batch production, is revealed as well. This MEMS process can mass-produce the sensors on silicon substrate in the ways of small size, low power, and high reliability. In addition to the gas or liquid concentration measurement, the present invention further discloses that the said sensor can also readily measure gas or liquid mass flow rate while record the concentration data, which is not viable by other related working principle.

15 Claims, 10 Drawing Sheets

Figure 2:
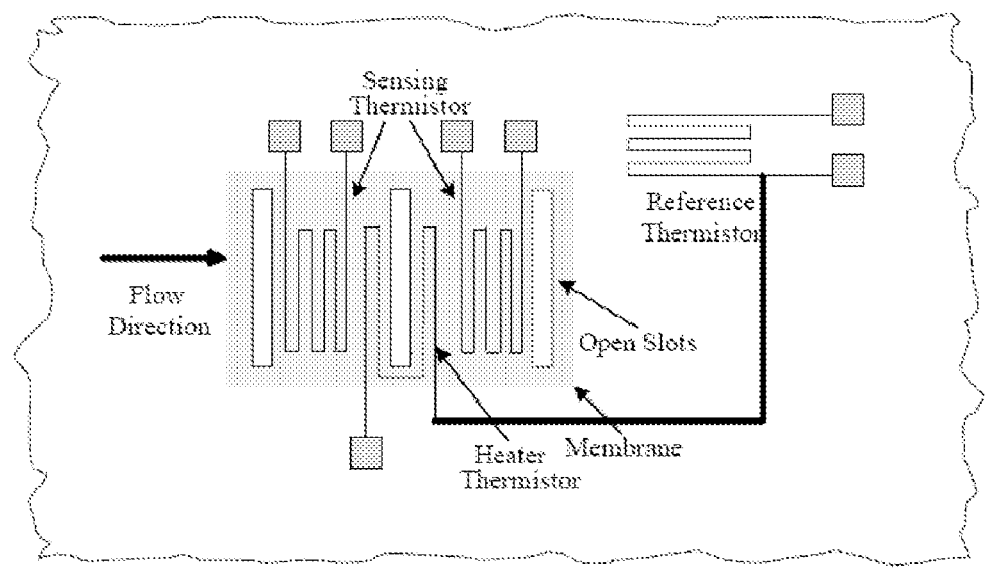

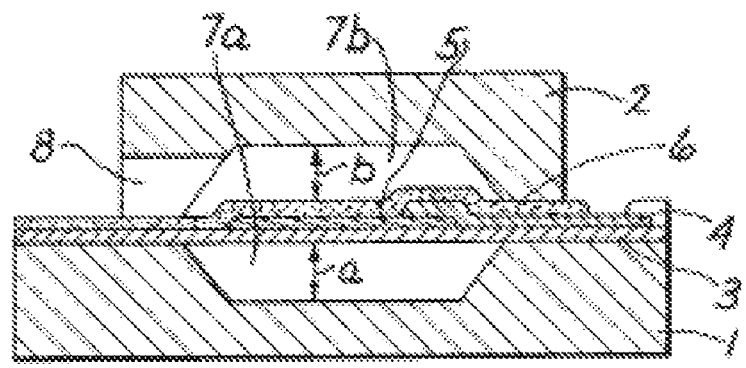
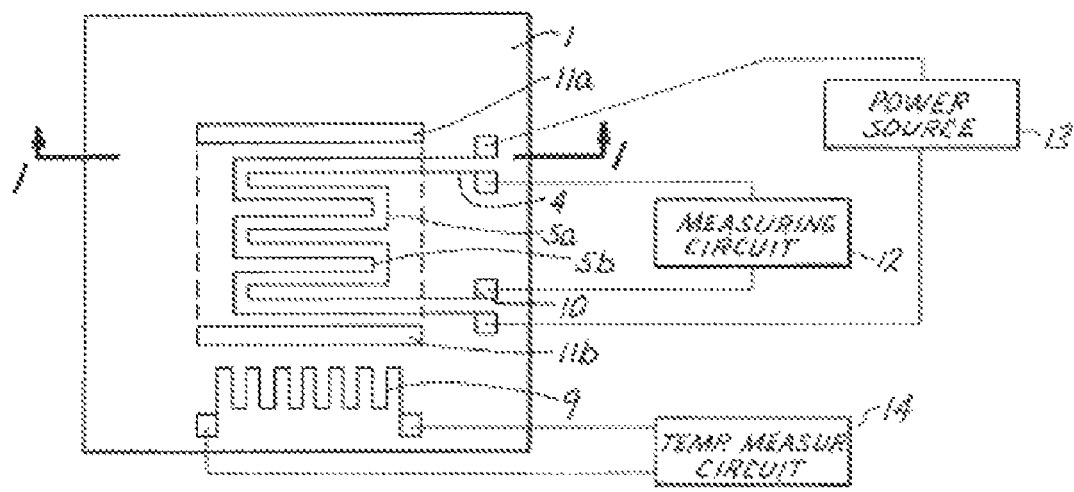
FIG. 1 (a) (Prior Art)

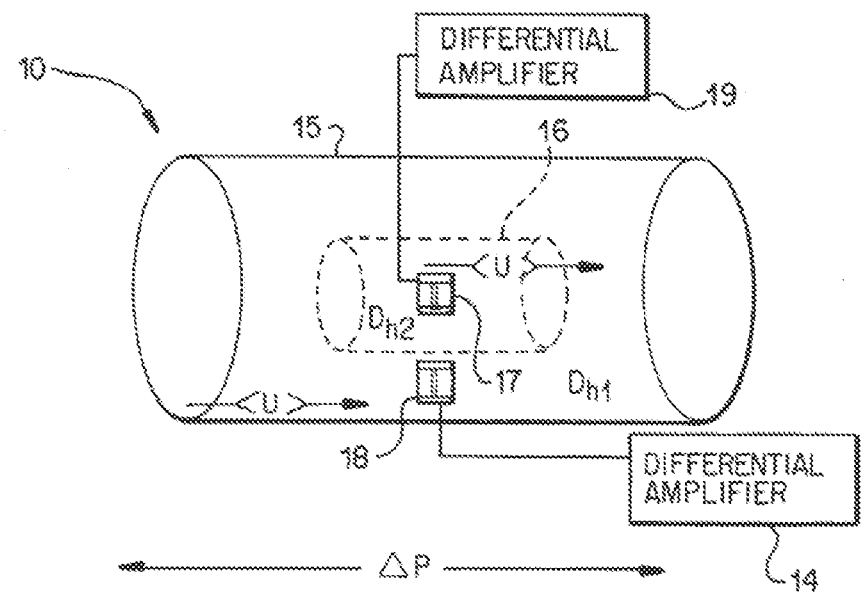
FIG. 1 (b) (Prior Art)
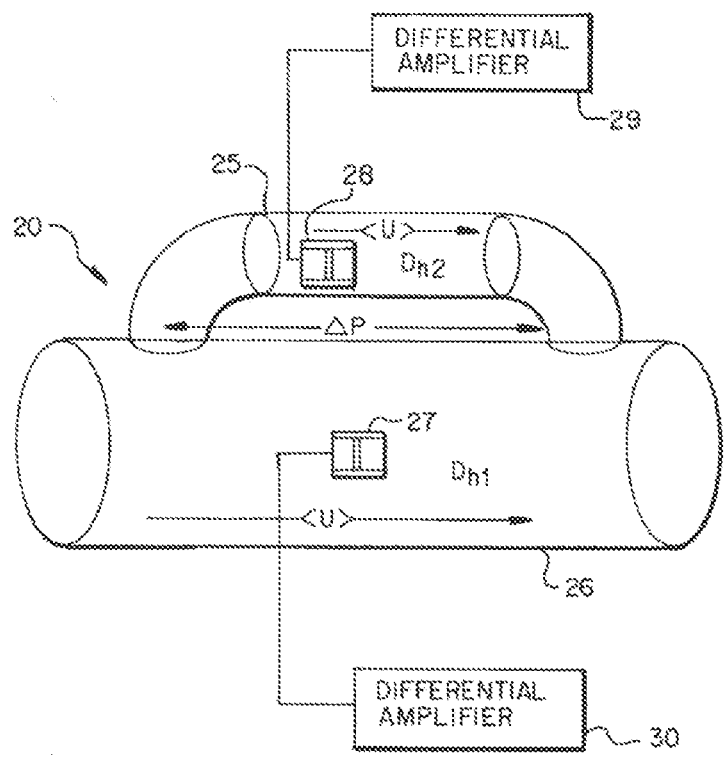
FIG. 1 (c) (Prior Art)

MICROMACHINED GAS AND LIQUID CONCENTRATION SENSOR AND METHOD OF MAKING THE SAME

BACKGROUND OF THE INVENTION

1. Field of the Invention

The present invention relates to a method and a device for measuring gas or liquid concentration in a binary mixture formality according to the preamble of the independent claims. The present invention also provides the methods and process for fabricating the device with micromachining or Micro Electro Mechanical Systems (MEMS) approach.

2. Description of the Related Art

Various gas or liquid concentration meters have been heretofore developed and commercially available on the market. The gas concentration sensors are broadly deployed in the fields such as oxygen, nitrogen, and other inert gas concentration detection. The liquid concentration sensors are applied on beverage, pharmaceutical, and chemical industries etc. The operation principles behind these commercial products are mainly based on the methods such as electrochemical reaction (H. Weyl and B. Wild, Measuring Device, U.S. Pat. No. 6,039,856; H. Dietz, Polarographic Oxygen Concentration Sensor and Method of Determining Oxygen Content in the Exhaust Gases of an Internal Combustion Engine, U.S. Pat. No. 4,356,065; G. Richter, G. Luft, U. Gebhardt, Method for Determining the Concentration of Sugar Using an Electrocatalytic Sugar Sensor, U.S. Pat. No. 4,366,033); optical refraction index (S. Akiyama, M. Fujiwara, T. Oida, et al., Gas Analyzer, U.S. Pat. No. 5,773,828; A. Robinovich, E. Diatzikis, J. Mullen, D. Tulimieri, Infrared Sensing of Concentration of Methanol's Aqueous Solution, U.S. Pat. No. 6,815,682); ultrasonic acoustic wave (A. Rabinovich and D. Tulimieri, Ultrasound Sensing of Concentration of Methanol's Aqueous Solution, U.S. Pat. No. 6,748,793); vibration resonate frequency (G. A. Michaels and H. Birangi, Gas Concentration Sensor and Control for Oxygen Concentrator Utilizing Gas Concentration Sensor, U.S. Pat. No. 5,917,135); capacitance detection (Richard K. Rader et al, Alcohol Concentration Sensor for Automotive Fuels, U.S. Pat. No. 5,255,656) and Coriolis force (F. C. Sittler, J. H. Crabtree, Fluid Flow Detector, U.S. Pat. No. 4,909,078) measurement.

U.S. Pat. No. 4,902,138 (Heinz-Dieter Goeldner, Measurement Component Concentration in a Gas Blend) reveals a device that a gas blend is introduced to a micro-machined chamber to indirectly determine its component concentration through measuring the thermal conductivity of gas blend (see FIG. 1(a)). The thermal conductivity sensor is composed of two finger-interlaced serpentine resistors wherein one of the resistors is heated up by a control circuit to elevate the temperature of proximate gas blend, and the other resistor is utilized to sense the temperature variation of gas blend. By measuring the gas blend temperature at different power level of heating resistor, the respectively collected data could apply to solve one set of equations, so the individual concentration of gas components can be determined. One of the drawbacks in this invention is the direct thermal conduction between the heating and sensing resistors could affect the accuracy of measurement since they are disposed so closely. In an ideal situation, the sensing resistor should only receive the heat conduction from gas blend. On the other hand, the sensitivity may become inferior if the heating and sensing resistors are separated further. Another drawback is that the invention can only limit to function in a static gas blend situation. The device in this invention could not work in a dynamic flow situation completely.

Zemel et al. teaches the approaches to measure mass flow and thermal conductivity simultaneously (Simultaneous Measurement of Gas Thermal Conductivity and Mass Flow, U.S. Pat. No. 5,463,899). Referring to FIG. 1(b), the system comprises two pyroelectric anemometers which are disposed respectively within each of the two conduits in a concentric arrangement. Each pyroelectric anemometer is connected to a differential amplifier. Since the ratio of the output signal of each pyroelectric anemometer in conduit 1 and conduit 2, $I_1$ and $I_2$ can be represented as $$\frac{I_2^2}{I_1^2} = x_{gas} \times const,$$

where $x_{gas}$ is gas thermal conductivity and const is a function of geometry which could be measured and decided. Therefore, the thermal conductivity of gas could be derived once $I_1$ and $I_2$ are obtained. The gas velocity can be correspondingly derived by formula from the known thermal conductivity $x_{gas}$. One of the downsides of this invention is the anemometer has to limit to pyroelectric type or the equation to derive the gas thermal conductivity is no longer true. Not like the conventional hot-wire anemometer, the pyroelectric anemometer needs high pyroelectric material (e.g. $LiTaO_3$) as substrate. The other drawbacks of this invention are coming from the requirements of double sensors, which are more costly, and the complexity of sensors disposition.

Therewith, the current invention shall have properties in many aspects of differentiation include dynamic metrology capability, faster response, lengthy lifetime, easiness of integration and lower cost.

SUMMARY OF THE INVENTION

It is therefore an object of the present invention to provide a process of a MEMS silicon concentration sensor applicable for concentration metrology of any fluid system of binary components with the advantages of the capability to synchronously measure flow rate of media if the said fluid system maintains a constant or variable flow conditions. The said concentration sensor shall also require a low power consumption that can be supplied by a battery. This object is reached by the independent claims.

In the present preferred embodiments, the silicon micromachined fluid concentration sensors based on the principles of anemometry and calorimetry are developed. The sensing elements of the concentration sensors mainly comprise four serpentine-shape thermistors which are made of same thin film materials. One of the thermistors is built as reference thermistor to monitor the ambient temperature while another one of the thermistors is functioned as heater thermistor. In most of cases, the resistance of reference thermistor is several times higher than the heater's. The heater thermistor is elevated to a constant temperature higher than the ambient temperature. A Wheatstone bridge circuit consisting of the heater and reference thermistors is designed to achieve constant temperature control of heater thermistor. Various materials with high TCR (temperature coefficient of resistance) such as Pt, Au, SiC, and TaN could be as the candidates for thermistors.

The heat dissipation rate of heater thermistor in a static fluid perceptibly depends on the fluid thermal properties which are affected by, for instance, fluid density, or the concentration of ingredients etc. Therefore, in order to keep the heater thermistor in a constant temperature mode, fluids with assorted densities or ingredient concentration will cause the heater thermistor in various heating power correspondingly. Thereby the output signal of heating power could be calibrated as the index of fluids density or ingredient concentration. In general, the heat loss of heater thermistor increases with the fluids density or ingredient concentration.

In the present preferred embodiments, the heater thermistor is standing on a thermally isolated thin film membrane as the reference resistor is solely located on top of substrate to keep good thermal conductivity to the environment. Both thermistors are encapsulated with a 0.3~0.5 micron thick dielectric film as passivation layer, which is also comprised in the suspended membrane. Above the dielectric film, a thin layer of fluorocarbon coating is deposited onto whole device to make the surface of device become hydrophobic and low surface energy. The thin hydrophobic fluorocarbon coating will significantly prevent alien particles or debris or liquid materials to stick on device surface which could degrade device operation. The cavity underneath the suspending membrane is fabricated by anisotropic bulk etching of the silicon substrate.

According to the present invention, the reference thermistor in a preferred embodiment is several times larger than the resistance of heater thermistor. With such embodiment, the power consumption in heater thermistor could be normally cut down 30~50%.

Since the heat dissipation rate of heater thermistor is not only a function of fluid thermal properties but also a function of fluid speed. In order to eliminate the effect of fluid speed, the fluid speed must be measured to compensate the concentration measurement in a dynamic flow. The fluid speed measurement in the present invention is carried by calorimetric flow sensors. It is usually implemented with a heater thermistor surrounded by two temperature sensing elements which are arranged either symmetrically or asymmetrically to the center of heater thermistor. Since the moving fluid continuously carries heat away from the heater thermistor, and thus to change the temperature distribution around the heater thermistor proximate area. The temperature variation between the upstream and downstream area of heater thermistor is measured by the temperature sensing elements. The output signal is normally recorded using a Wheatstone bridge circuit, in which the downstream and upstream sensing elements comprise two of its four branches. Various materials with high TCR (temperature coefficient of resistance) property such as Pt, Au, SiC, and TaN could be the candidates for temperature sensing elements.

In accordance with the present invention that provides the dynamic solution to eliminate the fluid flow effects that may otherwise adversely contribute to the said measurement, the heat dissipation rate of the heater thermistor in a fluid will perceptibly depend on the fluid thermal properties. The thermal property of the fluid is thus a function of the concentration of the fluid. For a fluid with known binary components, thereby the concentration of the fluid can be determined and represented by the power of heater thermistor while it is operated under a constant temperature mode and a prior calibration is conducted.

BRIEF DESCRIPTIONS OF THE DRAWINGS

FIG. 1(a)-(c): Illustration of the embodiments of several prior arts.

FIG. 2 Illustration of a preferred sensor topology: top view.

Figure 3:
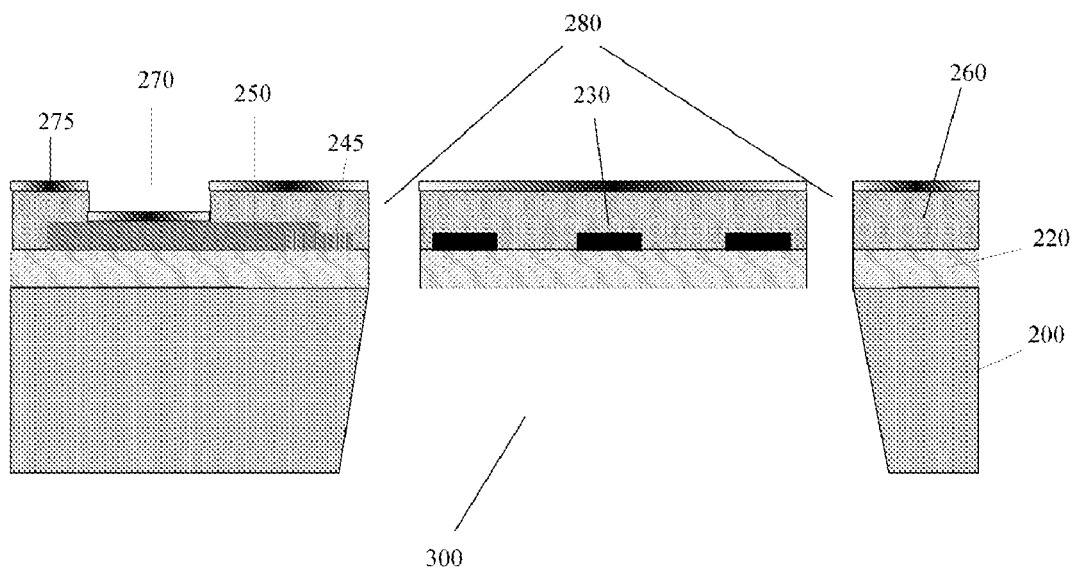

FIG. 3: A side view for a pictorial illustration of the method of making the preferred sensor.

FIG. 4(a) through FIG. 4(j) shows a process for forming a MEMS concentration sensor according to the preferred embodiment of the present invention.

Figure 5:
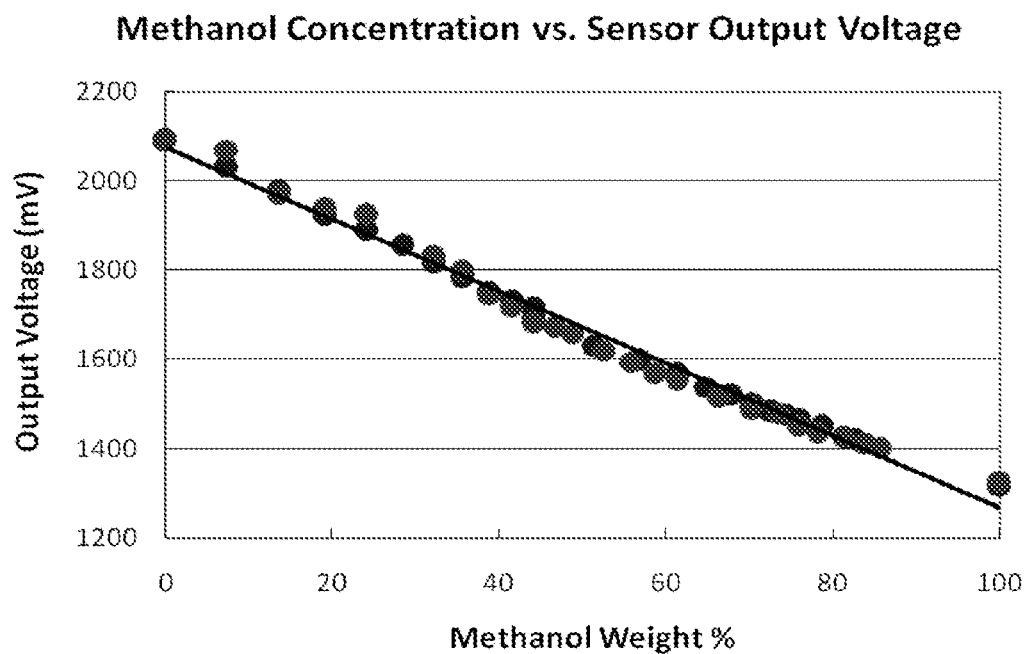

FIG. 5 exhibits the concentration sensor voltage output versus the methanol volume concentration in a water solution.

Figure 6:
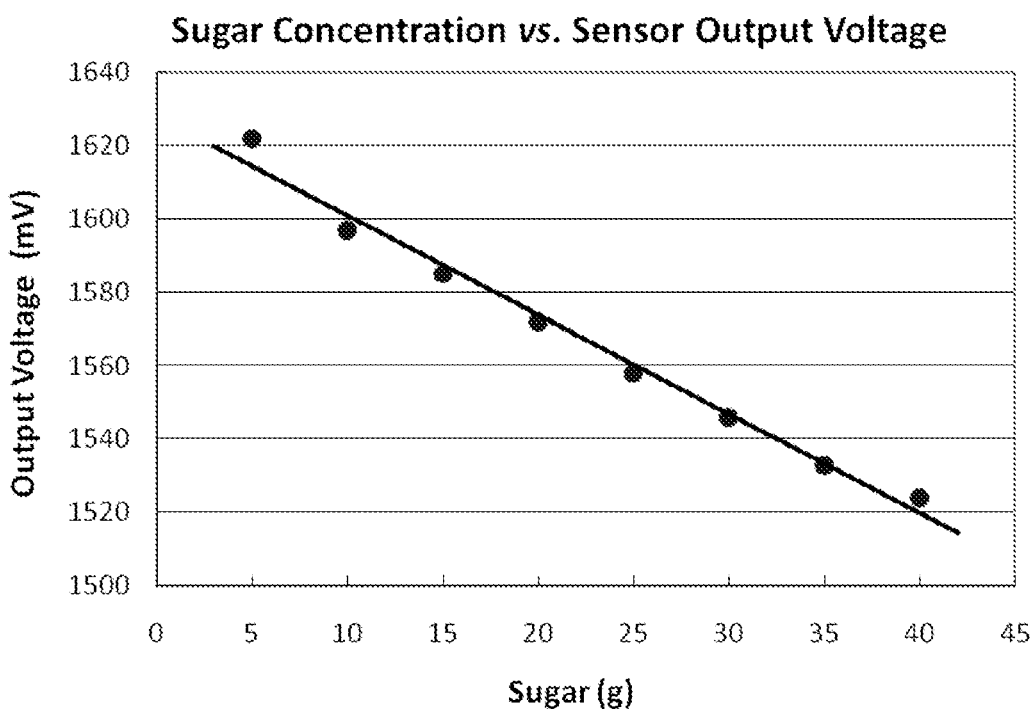

FIG. 6 shows the testing results of sensor outputs versus the weight percentage of sugar in water solution.

Figure 7:
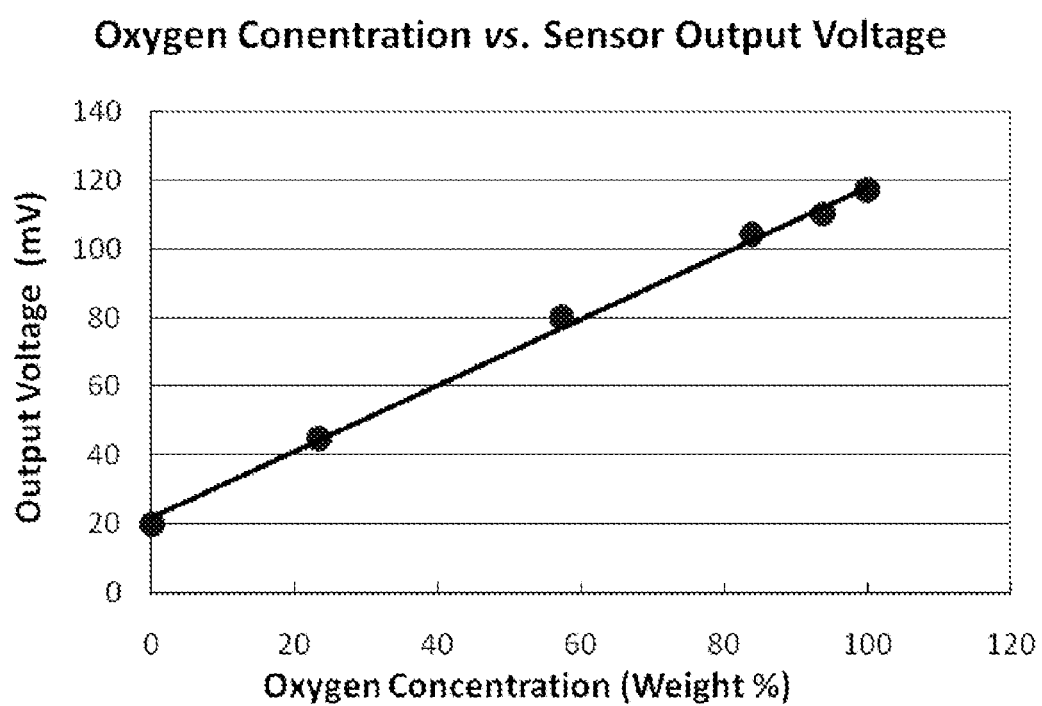

FIG. 7 demonstrates the output signal of sensor versus the oxygen concentration.

DETAILED DESCRIPTION OF THE PREFERRED EMBODIMENTS

FIG. 2 illustrates a top view of preferred sensor topology. The reference thermistor is used to measure the ambient temperature. The ambient temperature signal will be feedback to a closed-loop heater thermistor control circuit. The control circuit is to keep the heater temperature constantly above the ambient temperature. The sensing thermistors besides the heater thermistor are worked as the flow speed sensing elements.

The working principle behind the fluid concentration measurement in a binary-component system is primarily based on anemometry and calorimetry. Since the heater thermistor is operating under constant temperature mode, there are two major features will influence the output signal: the fluid concentration and the fluid flow speed. In a static flow, the fluid flow speed contribution will be nullified, whereas in the dynamic flow, the output signal is contributed by both. Therefore the fluid flow speed must be measured separately and be differentiated from the output signal. This is achieved by the prior calibration and computation algorithm, and thereafter the fluid concentration could be precisely acquired accordingly.

FIG. 3 depicts a side view for a pictorial illustration of the complete preferred sensor. From FIG. 4(a) through FIG. 4(i), they demonstrate a process for forming a MEMS concentration sensor according to the preferred embodiment of the present invention.

Figure 4:
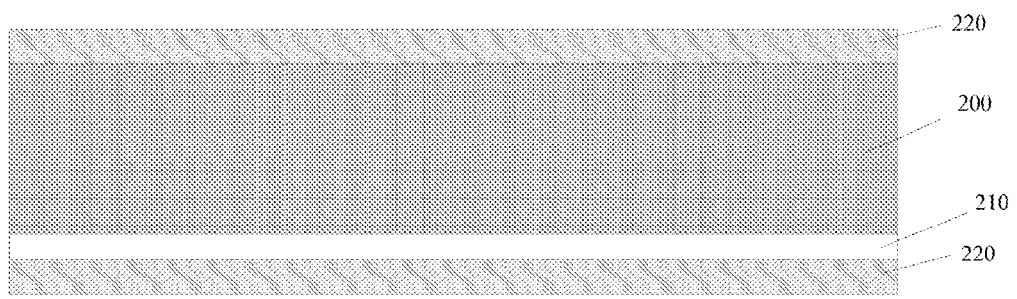
Figure 4:
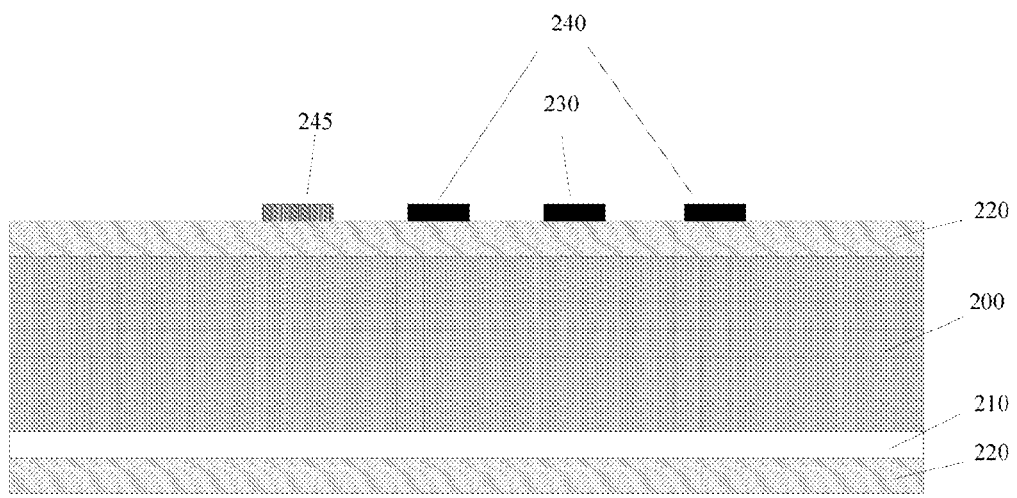
Figure 4:
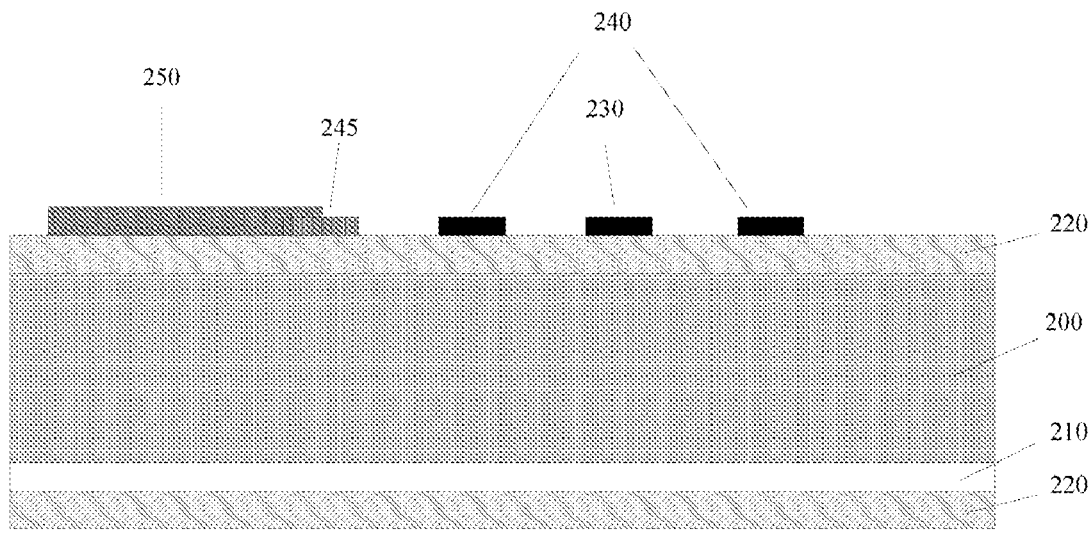
Figure 4:
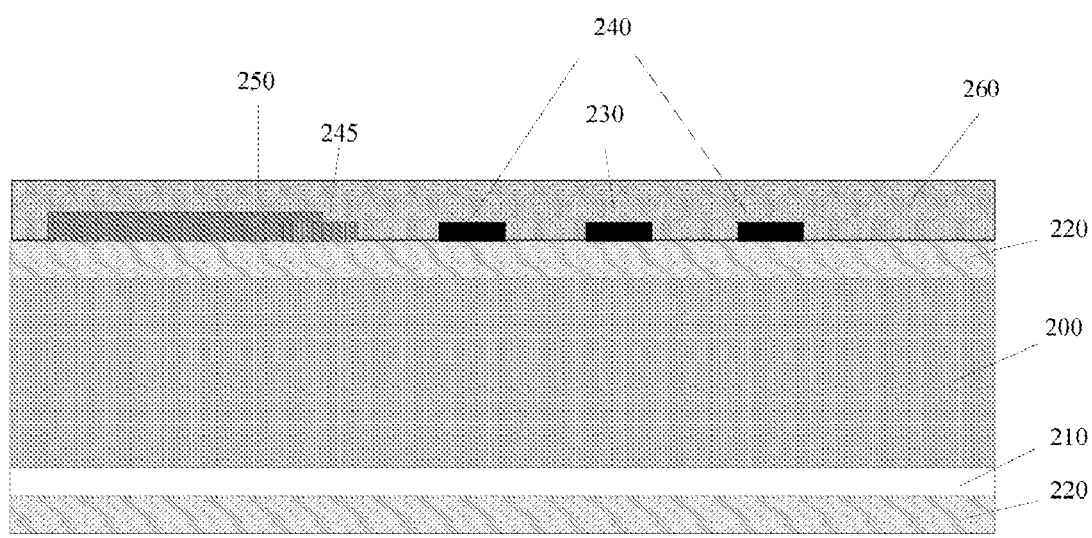
Figure 4:
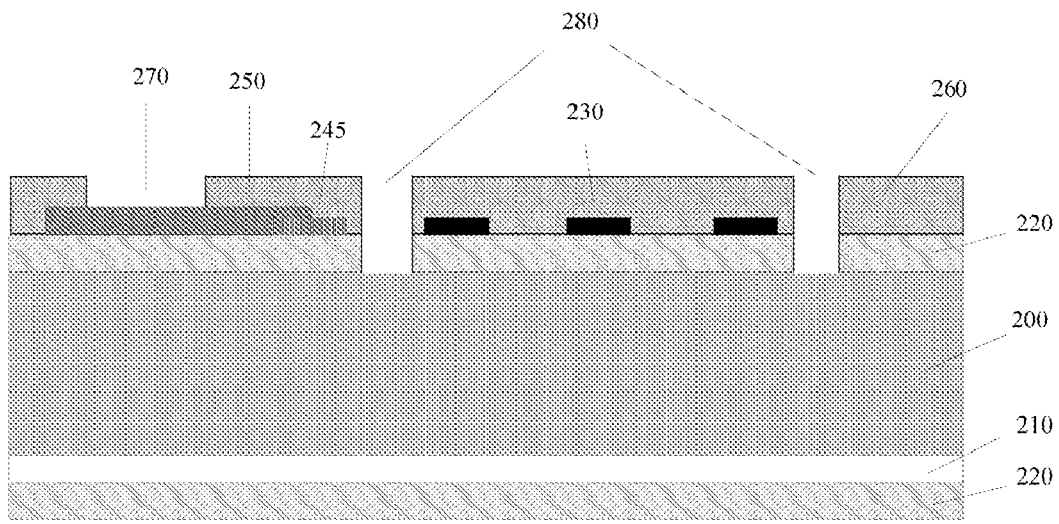
Figure 4:
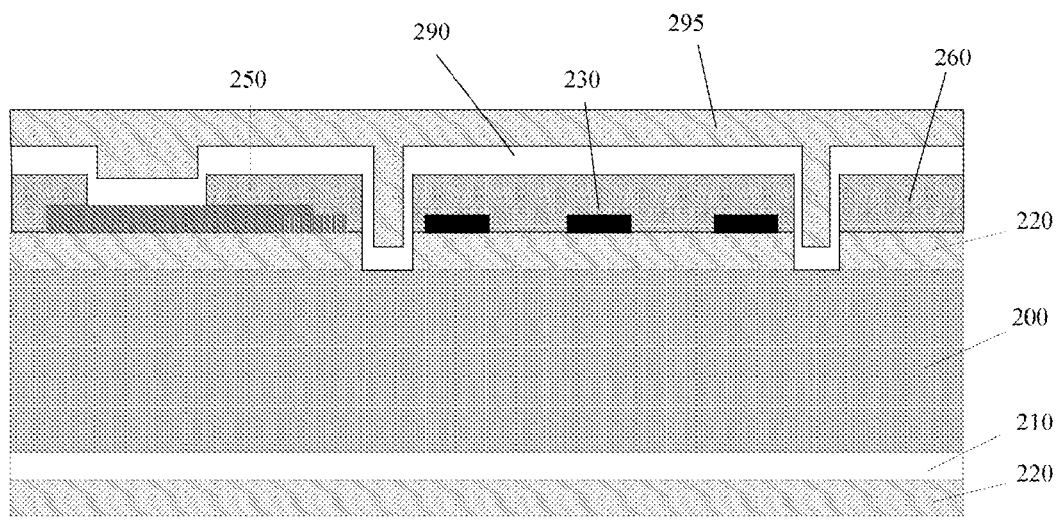
Figure 4:
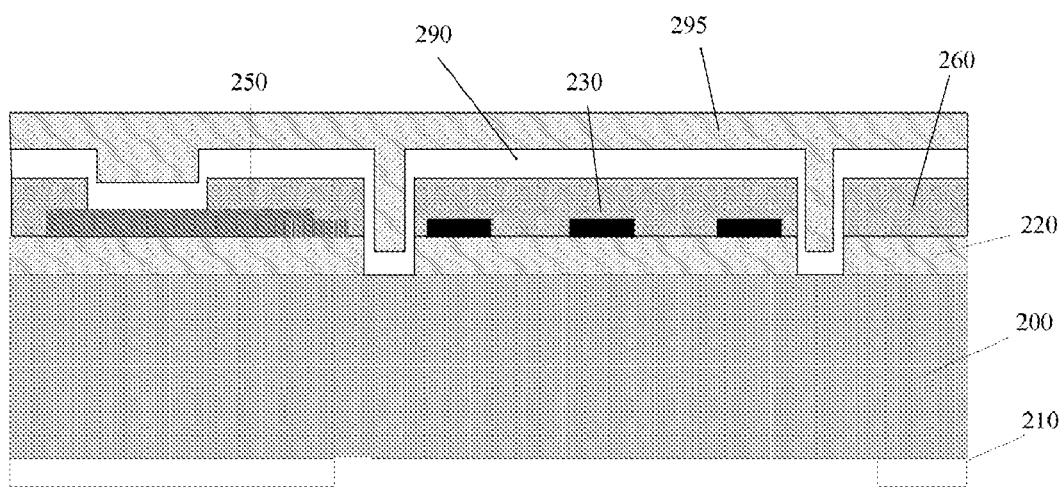
Figure 4:
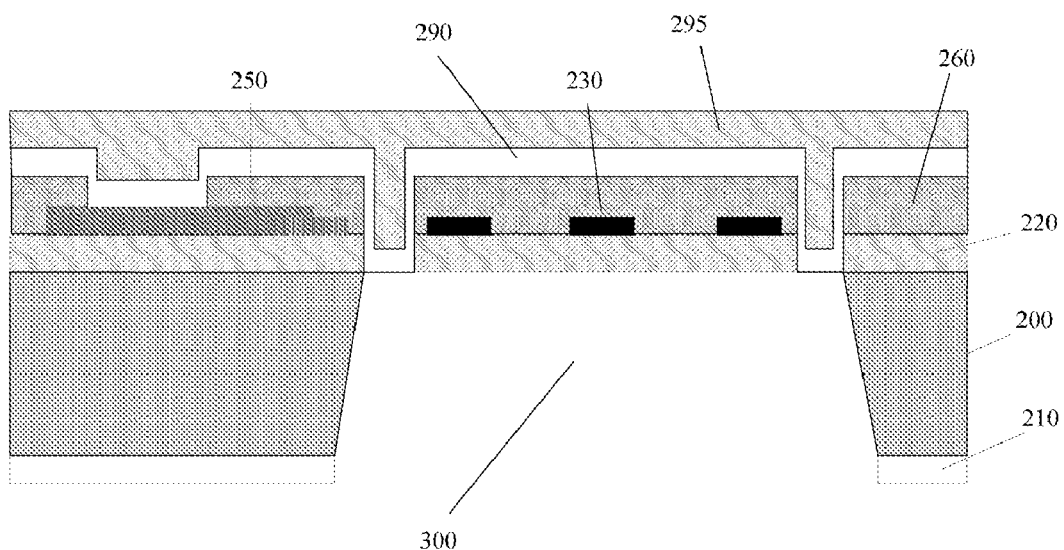
Figure 4:
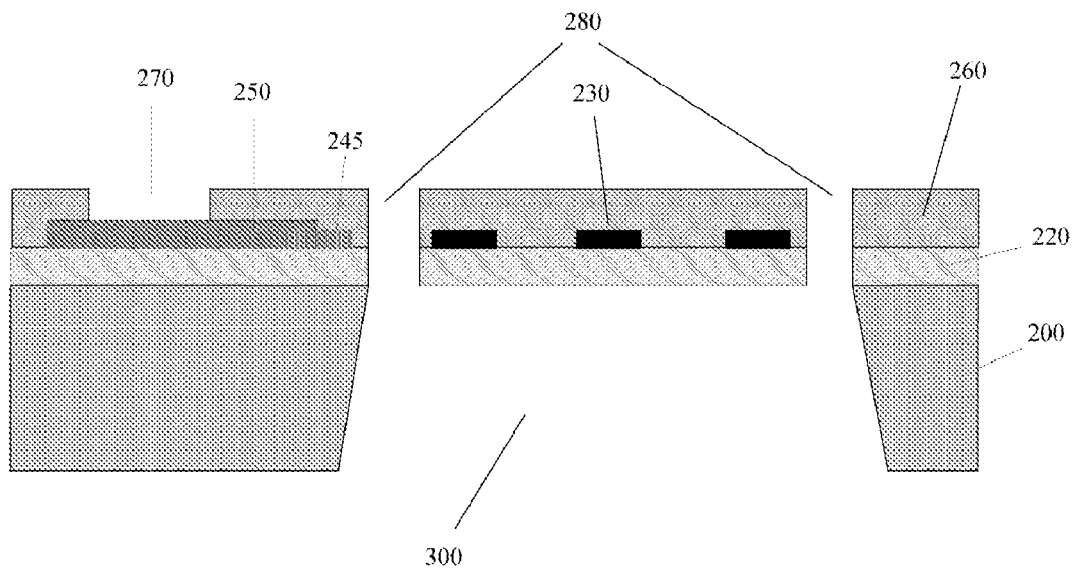
Figure 4:
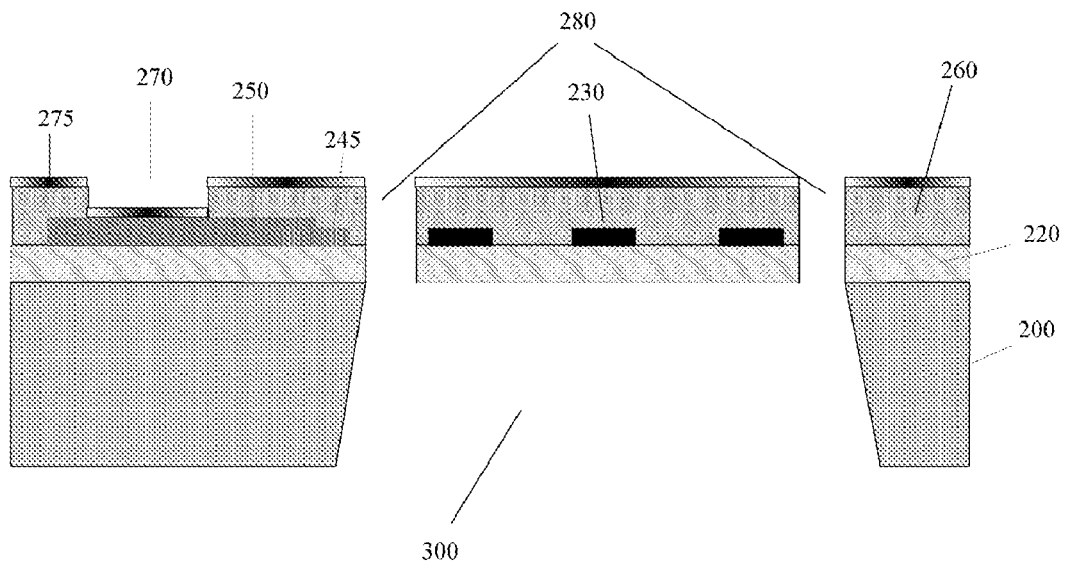

Referring to FIG. 4(a), thermal oxide layer 210 is formed on both side of the silicon substrate 200. And then the front side oxide layer is etched away, silicon nitride layer 220 is deposited on both side of the wafer. In view of FIG. 4(b), the heater thermistor 230, sensing thermistors 230, and reference thermistor 245 are all formed patterned by the film deposition and first photo mask procedure. The preferred thermistor materials are those with high temperature coefficient of resistance (TCR) such as platinum (Pt), gold (Au), silicon carbide (SiC), and tantalum nitride (TaN).

Then, in FIG. 4(c), a second masking and patterning procedure is performed to remove portions of the interconnection metal layer and form the interconnection circuit and the bonding pads 250. Subsequently referring to FIG. 4(d), a passivation layer 260, said dielectric thin film, for the overall processed substrate structure is deposited.

In the FIG. 4(e), a third masking and patterning procedure is performed to define the open-slots 270 in the membrane as well as the opening in the bonding pads. Subsequently, as shown in FIG. 4(f), two dielectric layers 290 and 295 are deposited on the front surface to protect the device during back-side bulk etching.

A fourth masking and patterning procedure on wafer backside is performed to define the opening for backside bulk etching as shown in FIG. 4(g). The backside bulk etching can be achieved by either dry etching—deep reactive ion etching (DRIE) or wet etching—KOH or TMAH etching. The KOH and TMAH solutions will etch the silicon along the <111> crystal plane and form a 54.74° slope in the sidewall of etching profile as shown in FIG. 4(h).

The front side protection layers (290, 295) and the backside masking layer 210 are removed after the completion of backside bulk etching. The completed device is shown in FIG. 4(i). According to the foregoing preferred embodiments, the suspending membrane 220 is to prevent the vertical heat conduction from heater thermistor to the bulk substrate. The open-slots on the membrane are formed to prevent the heat horizontally conducting to the bulk substrate as well. Thus, the device could reduce the power consumption of heater thermistor during device operation.

In the last step of process (see FIG. 4(j)), a very thin fluorocarbon coating 275 (5~15 nm) such as Teflon or Teflon-like film is deposited onto the surface of whole device by plasma enhanced deposition process. Since this thin passivation coating is hydrophobic and low surface energy, therefore it could significantly reduce the sensor surface sticking issues of alien particles and debris within the flow media. This coating layer is especially efficient to prevent the sticking of dust and moisture mixture onto device surface. Since the fluorocarbon film has low thermal conductive property, therefore it should be kept as thin as possible to remain the original functionality of device and to avoid the difficulties for wire bonding.

From the forgoing embodiments, the current invention of MEMS concentration sensor could be employed in many applications. In the FIG. 5, the test data is showing the concentration sensor voltage output versus the methanol volume concentration in a binary phase system (water and methanol solution). Referring to the FIG. 6, the chart illustrates the sensor voltage output is a linear response to the sugar weight concentration in water. By applying the sensor in a binary gas system (oxygen and nitrogen), as shown in the FIG. 7, the sensor output is turning out a linear function of the oxygen concentration.

The thermal dissipation rate of the heater thermistor in a static fluid system perceptibly depends on the fluid thermal properties which are affected by, for instance, fluid density, or the concentration of ingredients. As if the heater thermistor is operating under a constant temperature mode, the power applied to keep the heater in constant temperature under various media concentration could be used to represent the media concentration.

On the other hand, in the situation of dynamic fluid system, since the flow speed also affect the thermal dissipation rate of heater thermistor, therefore the sensing thermistor elements in sensor will function to measure the flow speed. The measured signals from the sensing thermistor elements will feedback to correct the output signal of concentration.

While the invention has been described in terms of what are presently considered to be the most practical and preferred embodiments, it is to be understood that the invention need not be limited to the disclosed embodiment. On the contrary, it is intended to cover various modifications and similar arrangements included within the spirit and scope of the appended claims which are to be accorded with the broadest interpretation so as to encompass all such modifications and similar structures. Therefore, the above description and illustration should not be taken as limiting the scope of the present invention which is defined by the appended claims.

We claim:

1. A fluid concentration sensor comprising:
   a heater thermistor connected to a first electronic circuit;
   a reference thermistor connected to said first electronic circuit with said heater thermistor together for measuring heat dissipating rate of said heater thermistor under a constant temperature operation thus to deduce concentration of a fluid; and
   two temperature sensing thermistors connected to a second electronic circuit for measuring a flow speed of said fluid, and wherein said flow speed of said fluid is applied to a microcontroller to calculate and eliminate influence of said flow speed of said fluid on said heat dissipating rate of said heater thermistor in a dynamic flow situation since said heat dissipating rate of said heater thermistor is depended on both said flow speed and said concentration of said fluid;
   wherein said heater thermistor and said two temperature sensing thermistors are disposed on a thermally isolated suspending membrane which is extending over a cavity and formed by silicon bulk etching from backside of a silicon substrate, and
   wherein said reference thermistor is disposed on a non-membrane region of said silicon substrate to measure ambient temperature.

2. The fluid concentration sensor of claim 1 wherein said silicon substrate is provided with a thermally isolating layer as said suspending membrane that is composed of low stress silicon nitride by low pressure chemical vapor deposition, and wherein a film stress range of said low stress silicon nitride is less than 150 MPa to avoid membrane cracking.

3. The fluid concentration sensor of claim 2 wherein said thermally isolating layer as membrane layer is made of preferred thermally isolating materials including silicon nitride, silicon dioxide.

4. The fluid concentration sensor of claim 1 wherein a first high temperature coefficient of resistance (TCR) layer is formed on said substrate.

5. The fluid concentration sensor of claim 4 wherein said high TCR layer is formed of preferred high TCR materials including platinum, gold, silicon carbide, tantalum nitride.

6. The fluid concentration sensor of claim 1 wherein said thermistors including said heater thermistor, said temperature sensing thermistors, said reference thermistors on said substrate are defined by a photolithography and etching procedure.

7. The fluid concentration sensor of claim 6 wherein said reference thermistor disposed on said substrate wherein said reference thermistor having a resistance ranging from three to twenty-five times a resistance of said heater thermistor.

8. The fluid concentration sensor of claim 1 wherein an interconnection of three metal layers is formed on said silicon substrate; portions of said three metal layers are removed by performing a photolithography and etching procedure to define interconnection and bonding pads; said three metal layers are included from bottom to top accordingly: chromium (Cr), platinum (Pt), and gold (Au); thickness of said chromium layer is from 100 to 200 angstroms as an adhesion enhancement layer in the bottom of said platinum layer; and thickness of said platinum layer is from 400 to 600 angstroms as a diffusion barrier layer between said chromium layer and said gold layer to prevent diffusion of gold molecules into said silicon substrate during some following high temperature process.

9. The fluid concentration sensor of claim 8 wherein a dielectric layer of silicon nitride in thickness from range of 3000 to 5000 angstroms is deposited by chemical vapor deposition as a passivation layer on front surface of said silicon substrate; portions of said passivation layer are removed by performing a photolithography and etching procedure to form contact holes on said bonding pads and two open-slots on said suspending membrane; and said two open-slots on said suspending membrane are fabricated to isolate heat transfer from said suspending membrane to said silicon substrate.

10. The fluid concentration sensor of claim 9 wherein one dielectric layer of silicon dioxide is overlaid on top of said passivation layer as a buffer layer; another dielectric layer of silicon nitride is consecutively deposited on top of said buffer layer as a protection layer of front surface of said silicon substrate; said protection layer is formed to avoid front surface damage of said silicon substrate during said silicon bulk etching as to form said thermally isolated suspending membrane; a dielectric layer of silicon nitride is deposited on backside of said silicon substrate as a silicon bulk etching mask layer; and said silicon bulk etching mask layer is patterned by performing a photolithography and etching procedure on said backside of said silicon wafer.

11. The fluid concentration sensor of claim 10 wherein said protection layer (silicon nitride), on front side of said silicon substrate is removed first by dry etching of a plasma with Sulfur Hexafluoride (SF6) gas; said buffer layer, silicon dioxide, is successively removed by wet etching of hydrofluoric acid (HF); said buffer layer (silicon dioxide) between said protection layer (silicon nitride) and said passivation layer (silicon nitride) is applied as an etching stopper layer for said dry etching of said plasma on said protection silicon nitride layer; and excellent etching selectivity of hydrofluoric acid (HF) between said buffer layer (silicon dioxide) and said passivation layer (silicon nitride) prevent overetching and damage of said passivation layer from etching process of said buffer layer.

12. The fluid concentration sensor of claim 1 wherein said temperature sensing thermistors further includes an upstream sensing thermistor and a downstream thermistor which are disposed on upstream and downstream locations relative to said heater thermistor on said thermally isolated suspending membrane.

13. The fluid concentration sensor of claim 12 wherein said temperature sensing thermistors disposed on said upstream and downstream locations of said heater thermistor could be arranged in a symmetrical or nonsymmetrical configuration related to center of said heater thermistor.

14. The fluid concentration sensor of claim 12 wherein said two temperature sensing thermistors are applied to measure said flow speed of said fluid independently and separately from said measurement of said heat dissipating rate of said heater thermistor and thus to eliminate said flow speed effects on said concentration measurement; therefore said fluid concentration sensor is able to function and measure said fluid concentration precisely in said dynamic flow situation.

15. The fluid concentration sensor of claim 14 wherein said flow speed of said fluid could be measured independently by said two temperature sensing thermistors; therefore the fluid concentration sensor could be functioned as a flow speed sensor as well.

* * * * *